US00PP28770P3

(12) United States Plant Patent
Hansen et al.

(10) Patent No.: US PP28,770 P3
(45) Date of Patent: Dec. 12, 2017

(54) ***MONARDA* PLANT NAMED 'PARDON MY LAVENDER'**

(50) Latin Name: *Monarda didyma*
Varietal Denomination: Pardon My Lavender

(71) Applicants: Hans A. Hansen, Zeeland, MI (US); Kevin A. Hurd, Austin, TX (US)

(72) Inventors: Hans A. Hansen, Zeeland, MI (US); Kevin A. Hurd, Austin, TX (US)

(73) Assignee: Walters Gardens, Inc, Zeeland, MI (US)

( * ) Notice: Subject to any disclaimer, the term of this patent is extended or adjusted under 35 U.S.C. 154(b) by 85 days.

(21) Appl. No.: 14/998,970

(22) Filed: Mar. 10, 2016

(65) Prior Publication Data

US 2017/0265369 P1 Sep. 14, 2017

(51) Int. Cl.
*A01H 5/02* (2006.01)

(52) U.S. Cl.
USPC ..... Plt./455

(58) Field of Classification Search
USPC ..... Plt./455
See application file for complete search history.

(56) References Cited

PUBLICATIONS

UPOV hit on *Monarda* plant named, 'Pardon My Lavender', CAPBR 16-8800, Jan. 22, 2016.*

* cited by examiner

*Primary Examiner* — Anne M Grunberg

(57) ABSTRACT

The new and distinct cultivar of ornamental bee balm plant named *Monarda didyma* 'Pardon My Lavender' has short, compact, branching stems and tight clumping habit, medium to dark green, numerous light lavender-pink flowers with excellent coverage and foliage highly resistant to powdery mildew.

1 Drawing Sheet

Botanical classification: *Monarda didyma.*
Variety denomination: 'Pardon My Lavender'.

BACKGROUND OF THE INVENTION

The present invention relates to the new and distinct cultivar of bee balm, botanically known as *Monarda didyma* 'Pardon My Lavender', and hereinafter also referred to solely as the cultivar 'Pardon My Lavender' or the "new plant". The new plant was selected from seed collected by the hybridizers on Oct. 7, 2009 from designated hybridizing garden of a nursery in Zeeland, Mich., USA, from *Monarda didyma* 'Petite Delight' U.S. Plant Pat. No. 10,784 as the female or seed parent and the male or pollen parent was uncontrolled and could have been any of the other parents in a large collection in the nearby vicinity. The plant was a single selection originally made in the summer of 2011 from the seeds that were collected and sown in the fall of 2009 and assigned the breeder code HK9-42-54. Further selection was completed in the trial fields of a nursery in Zeeland, Mich. in the summer of 2012. The plant has been asexually propagated originally in 2011 by stem cuttings at the same nursery in the greenhouses in Zeeland, Mich., and the subsequent asexually propagated plants found to be stable and identical to the original selection.

No plants of *Monarda* 'Pardon My Lavender' have been sold in this country, or anywhere in the world, prior to the filing of this application, nor has any disclosure of the new plant been made prior to the filing of this application with the exception of that which was disclosed within one year of the filing of this application and was either derived directly or indirectly from the inventors.

BRIEF SUMMARY OF THE PLANT

*Monarda didyma* 'Pardon My Lavender' is unique from its parents and all other bee balm plants known to the inventors. The nearest comparison varieties are the female parent 'Petite Delight' U.S. Plant Pat. No. 10,784, 'AChall' U.S. Plant Pat. No. 19,582, 'Balbalmurp' U.S. Plant Pat. No. 25,561 'Pardon My Purple' U.S. Plant Pat. No. 22,170, 'Purple Lace' U.S. Plant Pat. No. 25,615, 'Purple Rooster' (not patented), 'Sahin's Lavender' (not patented), and 'Vintage Wine' (not patented). 'AChall' is similar in height but the flower color of 'Pardon My Lavender' is lighter and more purple with less reddish-purple. 'Balbalmurp' requires two pinches to maintain a height of about 34.5 cm and the flower color is a much darker purple than 'Pardon My Lavender', which is about 35.0 to 45.0 cm tall without any pinching or growth retardants. 'Pardon My Purple' is about 30.0 cm tall without any pinching and the flower color is darker and more reddish purple than the new plant. 'Purple Lace' is about the same height as the new plant, but the flowers differ in the new plant being much lighter and less reddish-purple. 'Purple Rooster' is about twice the height of 'Pardon My Lavender' and has flowers that are much darker purple-red than the light lavender-pink of the new plant. 'Sahin's Lavender' has smaller diameter verticils with fewer flowers per verticil on plants about 120 cm tall. 'Vintage Wine' is darker and more reddish-violet in flower color and about twice the height of the new plant. Compared with the female parent 'Petite Delight' the new plant is slightly taller and broader in habit, and the flowers are light lavender-pink rather than pink-purple.

The following traits of *Monarda didyma* 'Pardon My Lavender' in combination distinguish it from all other Bee Balm known to the inventor:

1. Short, compact, winter-hardy, tight-clumping habit.
2. Medium to dark-green foliage that is highly-resistant to powdery mildew.
3. Large diameter heads of light lavender-pink flowers for a long period in summer showing excellent coverage.

BRIEF DESCRIPTION OF THE DRAWINGS

The photographs of the new plant demonstrate the unique traits of 'Pardon My Lavender' and the overall appearance of the plant at two-years old in the full sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
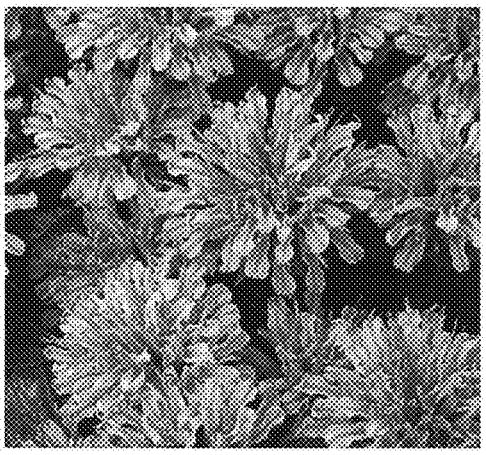
FIG. 1 shows a close-up of the flowers.
Figure 2:
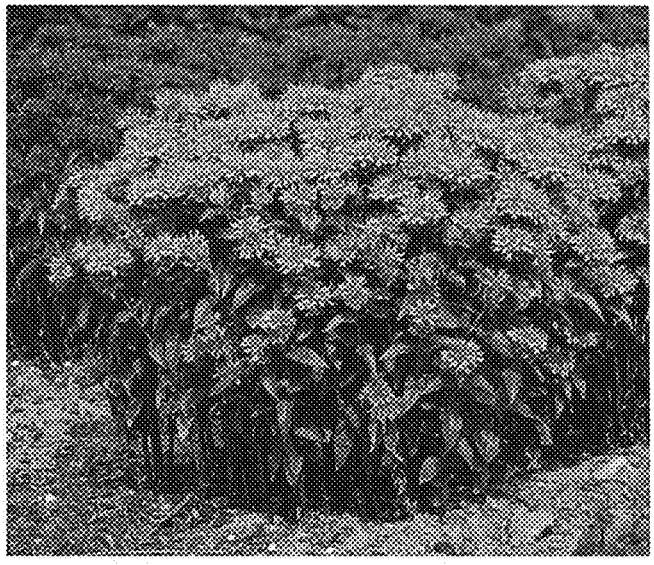
FIG. 2 shows the new plant in flower in the landscape.

The following descriptions and color references are based on the 2001 edition of The Royal Horticultural Society Colour Chart except where common dictionary terms are used. *Monarda didyma* 'Pardon My Lavender' has not been observed under all possible environments. The phenotype may vary slightly with different growing environments such as temperature, light, fertility, soil pH, moisture and maturity levels, but without any change in the genotype. The following observations and size descriptions are based on two-year old greenhouse-grown plants in gallon containers at a nursery in Zeeland, Mich. with supplemental fertilizer and water as needed but without plant growth regulators or pinching.

Botanical classification: *Monarda didyma.*

Parentage: Female (seed) parent is *Monarda didyma* 'Petite Delight' U.S. Plant Pat. No. 10,784; male (pollen) parent is unknown.

Plant habit: Winter-hardy herbaceous perennial, compact, producing several stems spreading by short rhizomes; 35 to 45 cm tall at flowering and 80 to 90 cm wide; flowering begins mid-summer in Michigan and continuing for about 5 to 8 weeks.

Propagation: Stem cuttings.

Time to produce finished crop in 3.8 liter pots: About 10 to 12 weeks; moderate rate of growth.

Root: Fine, fibrous and freely branching; color creamy white to tan depending on soil type.

Leaves: Simple, lanceolate, opposite, serrated, puberulent above and below; lustrous above, matte below; acute apex, rounded to cordate base; about 4.0 to 6.5 cm long by about 3.0 to 4.0 cm wide, average about 6.0 cm long and about 3.5 cm wide.

Leaf color: Young expanding leaves nearest RHS 138C on adaxial surface and on abaxial surface nearest RHS 138D; mature leaves between RHS 136A and RHS 139A on adaxial surface and on abaxial surfaces between RHS 138A and RHS 138B.

Foliage fragrance: Pleasantly herbal.

Veins: Pinnate; pubescent below with minute puberulent above, slightly sunken above and raised below.

Vein color: Mature leaves adaxial midrib and primary veins nearest RHS 145C, secondary veins nearest RHS 144A with tinting on midribs of some distal leaves nearest RHS 187A; mature abaxial midrib nearest RHS 145C with secondary veins nearest RHS 138B, secondary veins nearest RHS 145C; midrib and primary veins on emerging leaves adaxial surface nearest RHS 138C and secondary veins nearest RHS 138C; emerging leaves abaxial surface midrib and primary veins between RHS 145D and RHS 149D, secondary veins nearest RHS 145B.

Bracts: Between distal leaves and flowers; sessile; deltoid to lanceolate, with acuminate apex and truncate base; about seven per terminal verticillaster; average about 16.0 mm long and 10.0 mm wide.

Bract color: Abaxial and adaxial nearest RHS N144D with moderate tinting of nearest RHS N186C; and veins abaxial and adaxial of nearest RHS N144D with heaviest tinting of RHS 187A in the abaxial and adaxial midribs.

Petiole: Pubescent, slightly concaved above, about 3.5 mm long and 2.0 mm across.

Petiole color: Nearest RHS 138D both adaxial and abaxial.

Bracts: Between distal leaves and flowers; sessile; deltoid to lanceolate, with acuminate apex and truncate base; about seven per terminal verticillaster.

Bract color: Abaxial and adaxial nearest RHS 145A with veins with heavy tinting of nearest RHS N186C; and veins abaxial and adaxial of nearest RHS 187A.

Stems: Quadrangular, puberulent, densely pubescent at nodes; about 3.0 mm across at base and about 35.0 cm to 45.0 cm long.

Stem color: Between RHS 138A and RHS 138B with a tinting of nearest RHS N186C in upper portion, and base portion to nearest RHS 146C in light protected regions and between RHS N187C and RHS 187B in more intense light.

Branches: Quadrangular; beginning at about middle position on stems; about 12.0 cm long and 2.5 mm diameter at base.

Nodes: About 18 to 22 per stem; average internode length about 1.8 cm; color with more intense tinting of nearest RHS 187 B with stronger light, in areas of lower sun exposure between RHS 138A and RHS 138B with lighter tinting of nearest RHS N187B.

Flowers: Single, perfect, labiate flowers arranged in terminal verticillaster head about 7.0 cm across and 4.0 cm tall opening from the center and progressing outwardly and down; individual flowers persisting about 5 days in Michigan; numerous, about 80 flowers per head; self-cleaning.

Flower fragrance: Moderately spicy.

Buds one day prior to opening: Tubular, narrowly oblanceolate, arcuate downward; rounded apex; about 2.6 cm long and about 3.0 mm diameter.

Bud color: Between RHS N74C and RHS 72D in distal two-thirds with a lighter base of white, lighter than RHS N155D or RHS 155D.

Petals: Labiate, arcuate downward; fused into tube in basal about 1.8 cm and split in two in the distal 1.2 cm; upper lip forming hood about 3.0 cm long and about 2.5 mm diameter; lower lip about 3.5 cm long comprising three lobes including two side lobes about 2.0 mm long with rounded apex and center lobe about 4.0 to 5.0 mm long split in the distal 1.0 mm; both lips glandular and pubescent outer surfaces with fine hairs the same color as petals; both lips glabrous on inner surfaces.

Petal color: Color of all lips on both surfaces nearest RHS 72D as initially opening; lower lip developing to nearest RHS 76D both surfaces, and upper lip lightening on both surfaces to between RHS 75C and RHS 75D.

Androecium: Two.

*Filaments*.—Two, about 3.2 cm long by 0.5 mm diameter; color lighter than RHS 77D.

*Anther*.—Oblong elliptic, dorsifixed, longitudinal; about 2.2 mm long by about 1.0 mm wide; color nearest RHS N187B.

*Pollen*.—Abundant, elliptic to globose, less than 0.1 mm; color nearest RHS 11C.

Gynoecium: One per flower.

*Style*.—About 3.6 cm long by 0.25 mm diameter; color between RHS 75C and RHS 76C.

*Stigma*.—Split in two in the distal about 2.0 mm, about 0.25 mm in diameter; color between RHS 75D and RHS 76D.

*Ovary*.—1.0 mm by 0.75 mm, between RHS 143D and RHS 144B.

Sepals: Five, apiculate apex, base fused forming corolla about 9.0 mm long and 2.0 mm diameter; apex glandular and with minute hairs on abaxial surface, adaxial glabrous.

Sepal color: Apical margin nearest RHS 183C, distal two thirds of abaxial corolla surface nearest RHS 138C with tinting of nearest RHS 183C and veins of nearest RHS 183C; proximal half of abaxial corolla surface lighter than RHS 145D with veins also lighter than RHS 145D; adaxial surfaces same color as abaxial with veins remaining nearest RHS 138C.

Peduncle: Pubescent, stiff, strong, erect, quadrangular to about 0.3 cm across at base, average about 38.0 cm long.

Peduncle color: Between RHS 138A and RHS 138B with a tinting of nearest RHS N186C in upper portion, and base portion to nearest RHS 146C in light protected regions and between RHS N187C and RHS 187B in more intense light.

Fruit: Single nutlet, elliptical, about 1.0 mm long and 0.7 mm wide; color nearest RHS 202A.

Hardiness: The new plant grows best with plenty of moisture and adequate drainage; hardy to at least from USDA zone 4 through 8.

Disease and pest resistance: Demonstrated powdery mildew (*Sphaerotheca pannosa* var. *rosa*) resistance in side by side comparison at least equal that of 'Petite Delight' and better than 'AChall'.

We claim:

1. A new and distinct cultivar of ornamental bee balm plant *Monarda didyma* 'Pardon My Lavender', as herein described and illustrated.

* * * * *